(12) United States Patent
Liu et al.

(10) Patent No.: US 6,921,638 B2
(45) Date of Patent: *Jul. 26, 2005

(54) HYDROGEL-BASED MICROARRAY SIGNAL AMPLIFICATION METHODS AND DEVICES THEREFOR

(75) Inventors: Chang-Gong Liu, Buffalo Grove, IL (US); Abhijit Mazumder, Buffalo Grove, IL (US); Charles K. Brush, Whitefish Bay, WI (US); W. Travis Johnson, Chandler, AZ (US)

(73) Assignee: Amersham Biosciences AB, Uppsala (SE)

( * ) Notice: Subject to any disclaimer, the term of this patent is extended or adjusted under 35 U.S.C. 154(b) by 484 days.

This patent is subject to a terminal disclaimer.

(21) Appl. No.: 10/025,185

(22) Filed: Dec. 19, 2001

(65) Prior Publication Data

US 2002/0146730 A1 Oct. 10, 2002

Related U.S. Application Data

(63) Continuation-in-part of application No. 09/928,250, filed on Aug. 9, 2001, now Pat. No. 6,664,061, which is a continuation-in-part of application No. 09/344,620, filed on Jun. 25, 1999, now Pat. No. 6,372,813.

(51) Int. Cl.$^7$ .......................... C12Q 1/68; C07H 21/04; C08J 3/28
(52) U.S. Cl. .......................... 435/6; 536/23.1; 536/24.3; 536/24.32; 536/24.33; 522/114; 522/116; 522/117; 522/120
(58) Field of Search ...................... 435/6, 181; 436/532, 436/531; 522/114, 116, 117, 120, 121, 153; 527/200, 201; 536/23.1

(56) References Cited

U.S. PATENT DOCUMENTS

| | | | |
|---|---|---|---|
| 4,789,737 | A | 12/1988 | Miyoshi et al. |
| 4,935,339 | A | 6/1990 | Zahradnik |
| 5,196,306 | A | 3/1993 | Bobrow et al. |
| 5,371,241 | A | 12/1994 | Brush |
| 5,582,955 | A | 12/1996 | Wybourne et al. |
| 5,583,001 | A | 12/1996 | Bobrow et al. |
| 5,731,158 | A | 3/1998 | Bobrow et al. |
| 5,751,629 | A | * 5/1998 | Nova et al. ............ 365/151 |
| 5,808,044 | A | 9/1998 | Brush et al. |
| 5,888,733 | A | 3/1999 | Hyldig-Nielsen et al. |
| 5,932,711 | A | 8/1999 | Boles et al. |
| 5,981,734 | A | 11/1999 | Mirzabekov |
| 6,001,966 | A | 12/1999 | Pieken et al. |
| 6,087,102 | A | 7/2000 | Chenchik et al. |
| 6,096,508 | A | 8/2000 | Lemar et al. |
| 6,114,518 | A | 9/2000 | Pitner |
| 6,124,120 | A | 9/2000 | Lizardi |
| 6,133,429 | A | 10/2000 | Davis et al. |
| 6,203,989 | B1 | 3/2001 | Goldberg et al. |
| 6,320,041 | B1 | 11/2001 | Hogrefe |

FOREIGN PATENT DOCUMENTS

| | | |
|---|---|---|
| DE | 39 19 915 A | 12/1990 |
| EP | 0 386 644 A | 9/1990 |
| WO | WO 99/43688 | 9/1999 |
| WO | WO 00/18962 | 4/2000 |
| WO | WO 00/31148 | 6/2000 |
| WO | WO 01/01143 | 1/2001 |
| WO | WO 02/12566 | 2/2002 |
| WO | WO 00/31148 | 6/2002 |

OTHER PUBLICATIONS

Walker, M.A. "The Mitsunobu Reaction: A Novel Method for the Synthesis of Bifunctional Maleimide Linkers" Tetrahedron Letters, vol. 35, No. 5, 1994, pp. 665–668.

Booker–Milburn, K. I., et al. "Stereoselective Intermolecular '2+2! Photocycloaddition Reactions of Tetrahydrophthalic Anhydride and Derivatives with Alkenois and Alkynois" Tetrahedron Letters, vol. 55, 1999, pp. 5875–5887.

Elghanian, R., et al. "The use and evaluation of 2+2 photoaddition in immobilization of oligonucleotides on a three dimensional hydrogel matrix" Nucleosides, Nucleotides & Nucleic Acids, United States, 2001 Apr.–Jul., vol. 20, No. 4–7, Apr. 2001, pp. 1371–1375.

Rehman, F., et al. "Immobilization of acrylamide–modified oligonucleotides by co–polymerization" Nucleic Acids Research, Oxford University Press, Surrey, Great Britain, vol. 27, No. 2, Feb. 15, 1999, pp. 649–655.

Sproat, B., *Chemistry and applications of oligonucleotide analogues*, Journal of Biotechnology 41 (1995) 221–238.

*Covalent Coupling*, at http://www.exiqon.com/technology/covalent.htm.

Beaucage, S., *Oligodeoxyribonucleotides Synthesis: Phosphoramidite Approach* (Chapter 3), Methods in Molecular Biology, vol. 20, 33–61.

Jacobsen, N., M.Sc., *Technical Note: DNA Immobilizer*™ *at* http://www.exiqon.com/upload/lib DNA01.pdf.

Jacobsen, N., M.Sc., *Technical Note: DNA Immobilizer*™ *at* http://www.exiqon.com/upload/lib DNA02.pdf.

Verma, S., *Modified Oligonucleotides: Synthesis and Strategy for Users*, Annu. Rev. Biochem., 1998, vol. 67, pp. 99–134.

(Continued)

Primary Examiner—Kenneth R. Horlick
Assistant Examiner—Cynthia Wilder
(74) Attorney, Agent, or Firm—Royal N. Ronning, Jr.; Yonggang Ji; Stephen G. Ryan (57) ABSTRACT

Methods and devices for detecting nucleic acid and protein targets on hydrogel microarrays are disclosed. Fluorophores are incorporated into the targets and detected. A linear correlation between target concentration and signal amplitude is maintained through the elimination of active enzyme amplification.

38 Claims, 3 Drawing Sheets

OTHER PUBLICATIONS

Yamakazi et al., Journal of the American Chemical Society, 91, 520 (1969).

Cargill et al., Journal of Organic Chemistry, vol. 36, No. 10, 1971.

Caruthers, M., Chemical Synthesis of Deoxyoligonucleotides by the Phosphoramidite Method, Methods in Enzymology, vol. 154, pp. 287–313.

Alexa Fluor: Simply the Best and Brightest Fluorescent Conjugates, found at http://www.probes.com/media/publications/150.pdf.

Article, Amine–Reactive Probes, Molecular Probes Product Information (Revised: Dec. 26, 2001).

Article, Alexa Fluor® 532 Protein Labeling Kit (A–10236), Molecular Probes Product Information (Revised: Oct. 1, 2001).

Article, Alexa Fluor® Oligonucleotide Amine Labeling Kits, Molecular Probes Product Information (Revised: Apr. 6, 2001).

Shi, L., DNA Microarray (Genome Chip)–Monitoring the Genome on a Chip, found at http://www.gene–chips.com/.

Verma, S., Modified oligonucleotides: synthesis and strategy for users, found at http://www.ncbi.nlm.nih.gov:80.

PubMed search results for "phosphoramidite chemistry" from summary fields. Retrieved on 31 Mar. 2000. 59 hits found on 9 pages http://ww.ncbi.nlm.nih.gov:80.

STN structure search performed on Jul. 21, 2000 in Registry File.

* cited by examiner

HYDROGEL-BASED MICROARRAY SIGNAL AMPLIFICATION METHODS AND DEVICES THEREFOR

REFERENCE TO RELATED APPLICATIONS

This application is a continuation-in-part of U.S. Nonprovisional application Ser. No. 09/928,250, filed Aug. 9, 2001, now U.S. Pat. No. 6,664,061, entitled "The Use and Evaluation of A [2+2] Photocycloaddition in Immobilization of Oligonucleotides on A Three-Dimensional Hydrogel Matrix," which is a continuation-in-part of U.S. Nonprovisional application Ser. No. 09/344,620, filed Jun. 25, 1999, now U.S. Pat. No. 6,372,813 entitled "Methods and Compositions for Attachment of Biomolecules to Solid Supports, Hydrogels, and Hydrogel Arrays."

BACKGROUND

Chip based DNA microarrays are an integration of circuit fabrication technology and genetics. DNA microarrays consist of matrices of DNA arranged on a solid surface where the DNA at each position recognizes the expression of a different target sequence. Microarrays are used to identify which genes are turned on or off in a cell or tissue, and to evaluate the activity level under various conditions. This knowledge enables researchers to determine whether a cell is diseased or the effect of a drug on a cell or group of cells. These studies are critical to determine a drug's efficacy or toxicity, to identify new drug targets, and to more accurately diagnose illnesses, such as specific types of cancer. The technology is useful to classify tumors with the hope of establishing a correlation between a specific type of cancer, the therapeutic regiment used for treatment, and survival.

Expression microarrays are used to detect the presence of nucleic acids or polynucleotides generated, or expressed, by genes. These nucleic acids, or "targets," may be taken from any biological source, including healthy or diseased tissue, tissues that have been exposed to drugs, and pathogens. Because expression microarrays are often used to determine if a tissue is expressing different biomolecules than normal due to disease or drug treatment, the targets of interest are often nucleotides produced by these tissues.

Generally, single nucleotide polymorphism (SNP) microarrays are similar to expression microarrays, including their use of oligonucleotide probes and nucleic acid targets. However, differences can exist regarding how fluorescent labels are attached to the targets and how the microarrays are developed.

Another type of microarray, proteomic or protein arrays, are used to measure protein levels in cells. Generally, these arrays use antibodies as probes and cell lysates as targets. They are useful in high-throughput protein discovery, protein profiling, protein structure, and activity analyses, as well as protein-protein and protein-small molecule interaction studies.

Microarrays typically have biomolecules (probes) such as oligonucleotides or polypeptides attached to a polymer-coated solid support and arranged such that each of many small regions on the surface of the microarray contains a biomolecule that is at least slightly different from that of another region. When the microarray is contacted with a sample under appropriate conditions, components of the sample (targets) may bind to one or more biomolecules on the microarray. In order to detect the bound targets, the target typically contains a fluorescent molecule or dye that fluoresces when irradiated with light at its excitation wavelength. Fluorescent molecules are commonly referred to a "fluorophores" or "labels."

Multiple methods exist to incorporate fluorescent molecules into targets (See U.S. Pat. No. 6,203,989). A commonly used process is referred to as Tyramide Signal Amplification (TSA), which may be used to detect low concentrations of a molecule within a sample (See U.S. Pat. Nos. 5,731,158; 5,583,001; and 5,196,306).

Typically, during a TSA amplification, biotin is incorporated into the target of interest. Alkaline phosphatase (AP) or horseradish peroxidase (HRP) enzyme bound streptavidin or avidin is added. Tyromide labeled with a fluorophore is then added. The AP or HRP enzyme then incorporates multiple labeled tyramides at the probe site, thereby increasing or amplifying the number of fluorophores at the probe/target site.

TSA methods generate a large number of fluorescent labels at the probe/target site due to the enzymatic action of the AP or HRP. Thus, the actual number of fluorophores at the probe/target site is not linearly related to the number of probe/target bindings which occur, but is dependent on the activity of the enzymes.

When microarrays are formed using hydrogels as the solid support coating, TSA methods result in large levels of background noise, thus providing a poor signal to noise ratio. Such high levels of background noise are likely a product of variation in the enzymatic reaction. Therefore, there is a need for high-sensitivity target detection methods for use with hydrogel microarrays that provide a good signal to noise ratio.

BRIEF SUMMARY

Methods of detecting a target nucleic acids or proteins are provided. The target nucleic acid may be a cDNA or a cRNA molecule and the proteins may be in the form of cell lysate. Generally, the target nucleic acid or protein is created such that it contains a first member of a binding pair (for example, biotin of the biotin/streptavidin binding pair).

The target is then applied to a hydrogel matrix on which a plurality of probes is attached under conditions that allow hybridization of the target molecule to one or more complimentary probes. The hybridized target is then contacted with a fluorescently labeled second member of a binding pair (for example, streptavidin). Hybridization of a target molecule to a probe on the hydrogel can be detected by the existence of a fluorescent emission in the region of the probe when the fluorescent label is excited.

Devices for detecting a target nucleic acids or proteins are provided. An exemplary device comprises a 3D hydrogel matrix having a plurality of probes attached. Hybridized to one or more probes is a target nucleic acid or protein comprising a first member of a binding pair. The device further comprises a fluorescently labeled second member of a binding pair bound to a first member within the target nucleic acid or protein and an emitter and photodetector for exciting and detecting fluorescence from the fluorescent molecule.

Also provided are methods for detecting a single nucleotide polymorphism. Generally, such methods include hybridizing a target nucleic acid to a probe attached to a hydrogel matrix. The probe is designed to terminate immediately 3' of the single nucleotide polymorphism. The probe is then extended by a single nucleotide comprising a first member of a binding pair. The presence of the incorporated nucleotide is then detected by contacting the first member of a binding pair with a second member of the binding pair comprising a fluorescent molecule and detecting fluorescence.

DETAILED DESCRIPTION

The devices and methods for detecting nucleotides, nucleotide polymorphisms, and proteins in accord with the present invention are based on the binding of a fluorescently labeled target of interest to a probe situated on a hydrogel microarray.

Typically, microarrays are a collection of probe binding sites at known physical locations bound on a surface. By positioning tiny specks of probe molecules at known surface locations and then exposing a collection of target molecules to the probes, selective hybridization or binding occurs between specific probes and targets. For example, because adenine only binds to thymine, a thymine probe will selectively bind to an adenine target.

Once probe/target binding occurs, unbound targets are washed away and the microarray is analyzed to determine which targets have bound at what probe locations on the microarray. Because a plethora of different probes can be deposited on a single microarray, numerous types of binding analyses can be simultaneously performed.

Targets

Expression microarrays are used to detect the presence of nucleic acids or polynucleotides generated, or expressed, by genes. These nucleic acids, or "targets," are preferably polynucleotides such as RNA (including mRNA) and DNA, or modifications thereof, and more preferably mRNA. They may be taken from any biological source, including healthy or diseased tissue or cells, and tissues or cells that have been exposed to drugs, and pathogens. Because expression microarrays are often used to determine if a tissue is expressing different biomolecules than normal due to disease or drug treatment, the targets of interest are often polynucleotides produced by these tissues. When targets include mRNA, probes preferably include polynucleotides.

Protein microarrays are similar to expression microarrays, except they are used to detect the presence and/or levels of proteins in cells. They may detect any portion of a protein and preferably use cell lysates as targets and antibodies as probes. When targets include proteins, probes are typically antibodies, but can also be DNA or proteins under some circumstances.

Labels

In an expression or protein microarray, the targets of interest are labeled with molecules that fluoresce when irradiated with light at a known wavelength, or fluorophores, including dyes or other compounds. The fluorescent emission from the labeled targets allows their detection by spectroscopic methods. By irradiating the microarray with light at the excitation wavelength or wavelengths of the dyes used, the labeled targets may be detected. By placing different dyes on different targets, multiple determinations may be made from a single microarray.

In addition to determining the presence of a specific target, microarrays may be used to simultaneously make a quantitative determination of the detected targets. This is possible by incorporating "probe standards" into the microarray which selectively bind to specific labeled "target standards," but do not interfere with analyte probe/target binding. Generally, the labels incorporated into the target standards fluoresce or emit at a different wavelength than the labels incorporated into the analyte targets. Preferred target standards are yeast mRNA and bacterial mRNA, or combinations thereof. Yeast mRNA is most preferred.

The literature contains examples of many fluorescent dyes suitable for labeling the targets, including fluorescein, rhodamine, resorufin, coumarin, and cyanine. Preferred labels include those sold under the tradename ALEXA FLUOR. These fluorophores are dyes with trade secret compositions which may be purchased from Molecular Probes, Inc. (849 Pitchford Avenue, Eugene, Oreg. 97402-9165 USA). Preferred ALEXA FLUOR dyes include ALEXA-532, ALEXA-633, and ALEXA-647. Most preferred is ALEXA-647, which absorbs well into the "red" region of the spectrum.

Other preferred labels include the cyanine dyes prepared with succinimidyl ester reactive groups, such as Cy-3, Cy-5, Cy-5.5. The number immediately after the "Cy" indicates the number of bridge carbons. The number following the decimal point indicates a unique dye structure, which is determined by the substituents on the structure. Cy-3, Cy-5, and Cy-5.5 are available from Amersham Pharmacia Biotech (Piscataway, N.J., USA). Of the cyanine dyes, Cy-3 is most preferred.

Once the labeled targets hybridize with the probes, the labels are detected by scanning the microarray in an appropriate spectrophotometer to collect fluorescence position and optionally, intensity data. If Cy-3 is used as the fluorophore for the targets, measuring is conducted at about 532 nanometers. If ALEXA-647 is used, the array is excited at 633 nanometers and measured at between 665 and 675 nanometers.

Other scanning wavelengths are possible, as dictated by the labels used. A preferable scanner is an AXON SERIES A, available from AXON INSTRUMENTS, Union City, Calif., or equivalent. For quantitative analysis, the scanner, or optional processor, computes the intensity ratio of target to a target standard fluorescence.

SNP

Generally, single nucleotide polymorphism (SNP) microarrays are similar to expression microarrays, including their use of oligonucleotide probes and nucleic acid targets. However, significant differences can exist regarding how fluorescent labels are attached to the targets. For an expression microarray, the targets are generally labeled prior to their dispersion on the microarray. Alternatively, for an SNP array in which the targets are not previously labeled, the target solution contains non-labeled targets, an active enzyme, a fluorescently labeled carrier, and optionally, target standards.

While expression microarrays rely on selective probe/target binding to generate a fluorescent pattern on the array, SNP microarrays rely on enzyme selective single base extension (SBE) of a selected probe/target complex. During development of the SNP microarray, the targets hybridize to their respective probes to form a complex, typically having a double-helix structure. If an appropriate complex is recognized by the active enzyme or nucleotide, it transfers the label by a SBE reaction from the carrier to the complex. Preferable nucleotides include dideoxynucleotides and acyclonucleotides. Thus, fluorescent probe/target sites are selectively created. The SNP microarray may then be washed and scanned similarly to an expression array to confirm the presence of a specific target, and optional quantitation, if probe and target standards are used.

Fluorophore Incorporation

Targets are detected because they are labeled with a fluorophore, such as a fluorescent dye. Such incorporation relies on the binding of at least a first and a second binding member. For expression and protein microarrays, a first binding member of a binding pair is attached to the target. For SNPs, the first binding member may be attached to the target in the same manner as in expression arrays or may become attached to the probe-target duplex after hybridization through enzymatic extension using a polymerase and a nucleotide which is connected to the first binding member. This attachment may be by chemical or photochemical means. A general description of binding member attachment to probes may be found in Levenson C. et al., "Biotinylated psoralen derivative for labeling nucleic acid hybridization probes." Methods Enzymol. 1990; 184; 577–83.

First Binding Members

First binding members of the current invention are small molecules that may be attached to oligonucleotide, antibody, DNA, RNA, modified DNA and RNA, and protein targets. First binding members which are preferred for attachment to the targets include biotin, digoxygenin, and bromouridine. Most preferred is biotin.

Second Binding Members

When the first binding member of a binding pair is contacted with a second binding member, the binding members attach to form a bound pair. Preferred second binding members include streptavidin (SA), avidin, biotin antibody, bromouridine antibody, and digoxygenin antibody. Most preferred is streptavidin. Preferably, one or more fluorophores are bound to the second binding member. More preferably, three to four fluorophores are bound to the second binding member. Most preferably, the second binding member is streptavidin with greater than one fluorophore attached.

Linear Amplification

In order to accurately detect targets hybridized onto the probe sites of a microarray, large fluorescent emissions are desirable. Greater intensity emissions from a single hybridized probe/target site results in more accurate and reproducible detection and optional quantitation analysis. Additionally, large emission signals require smaller amounts of target analytes and less costly and complex detection systems.

While TSA methods produce large emission amplitudes, the amplitude produced is not linearly related to the number of probe/target hybridizations. This lack of linearity is due to the intervening enzymatic reaction which incorporates the fluorophores at the probe/target site. Instead of emission amplitude being linearly related to the actual number of bound targets, it is based on the number of enzymatically cleaved targets. Dependent on this cleavage reaction, emission amplitude is affected by any environmental conditions which affect enzymatic cleavage, including temperature, reaction time, and the physical and chemical properties of the substrate to which the target is bound.

Figure 1:
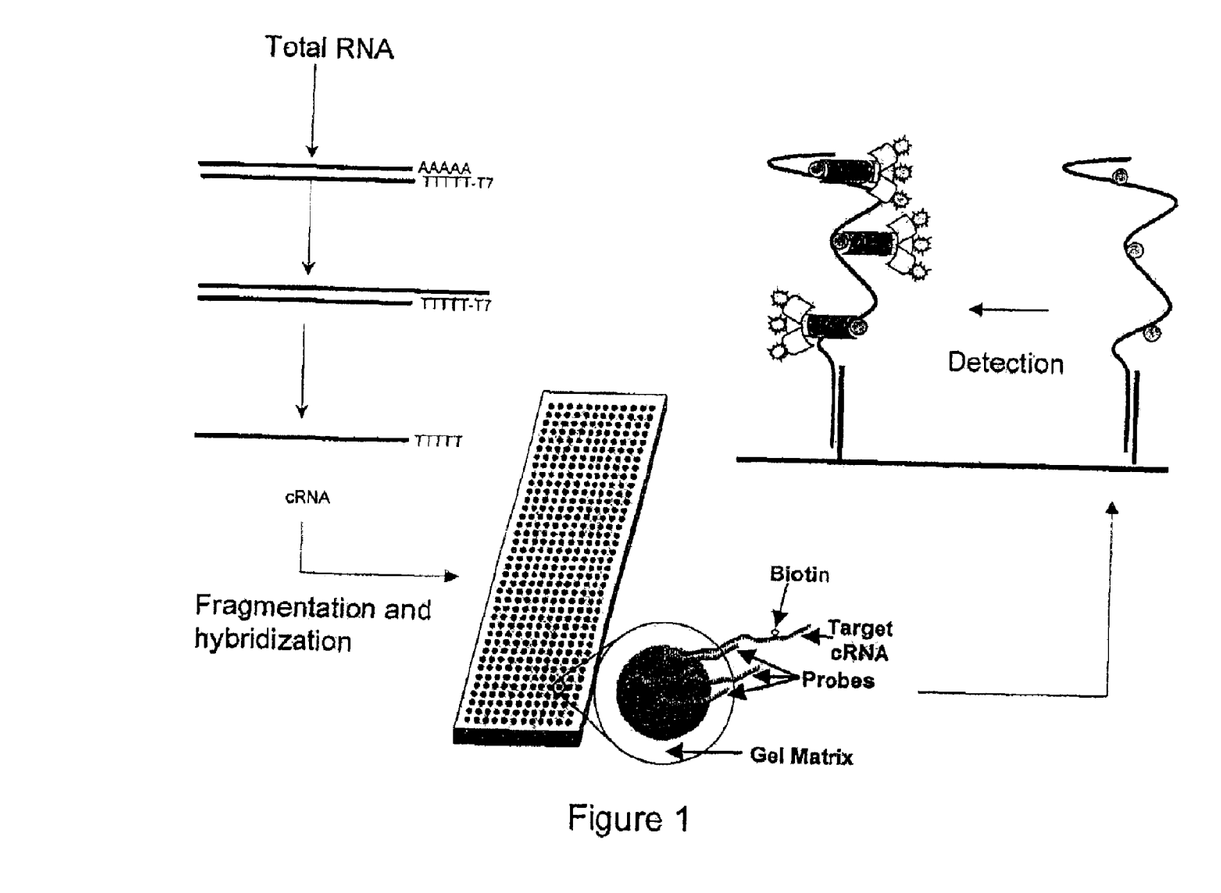
FIG. 1 shows a depiction of an assay wherein the biotinylated targets, after hybridization to the oligonucleotide probes, bind the streptavidin-fluorophore conjugate, generating enhanced signal because each conjugate contains 3 to 4 fluorophores.
Figure 2:
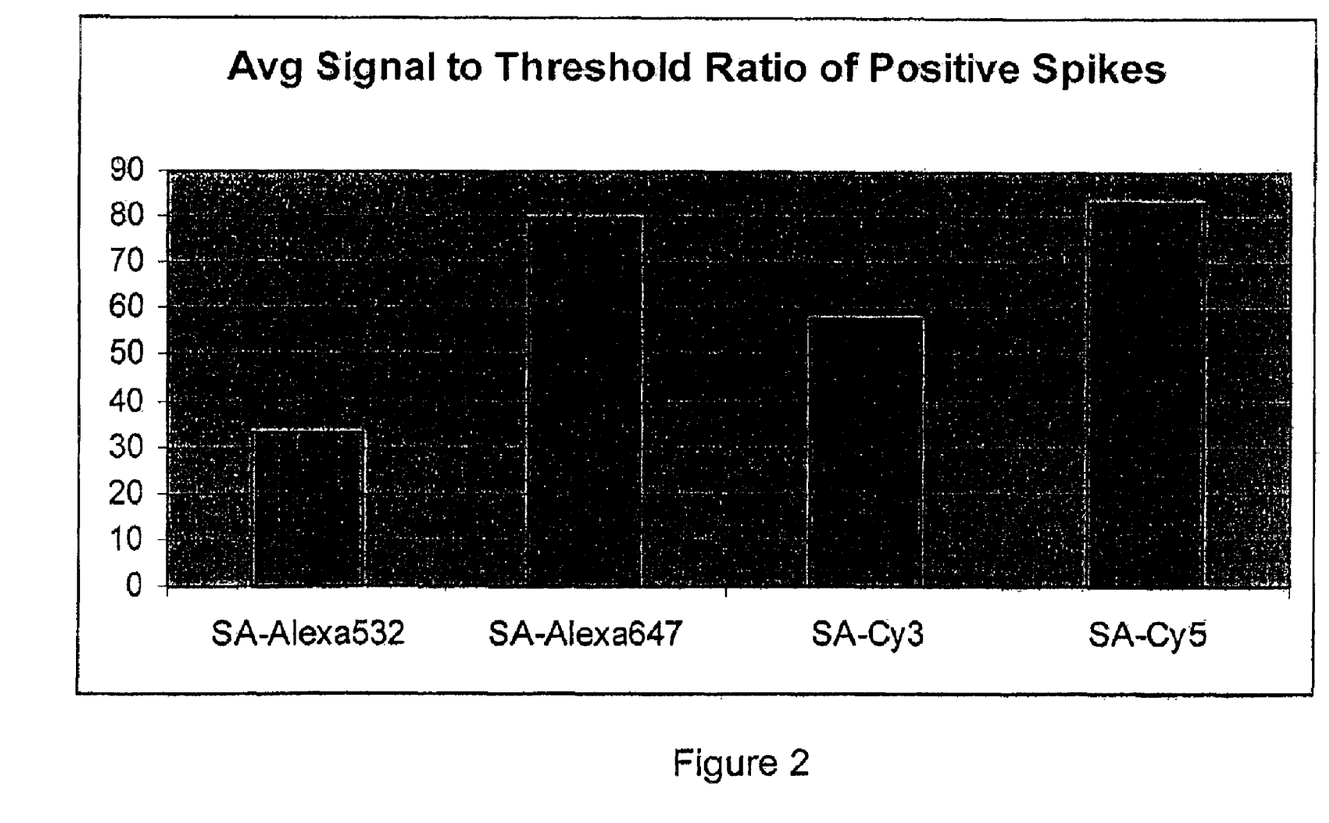
FIG. 2 shows a comparison of several different streptavidin-fluorophore conjugates. In general, those which emit in the red region show the best signal to noise.
Figure 3:
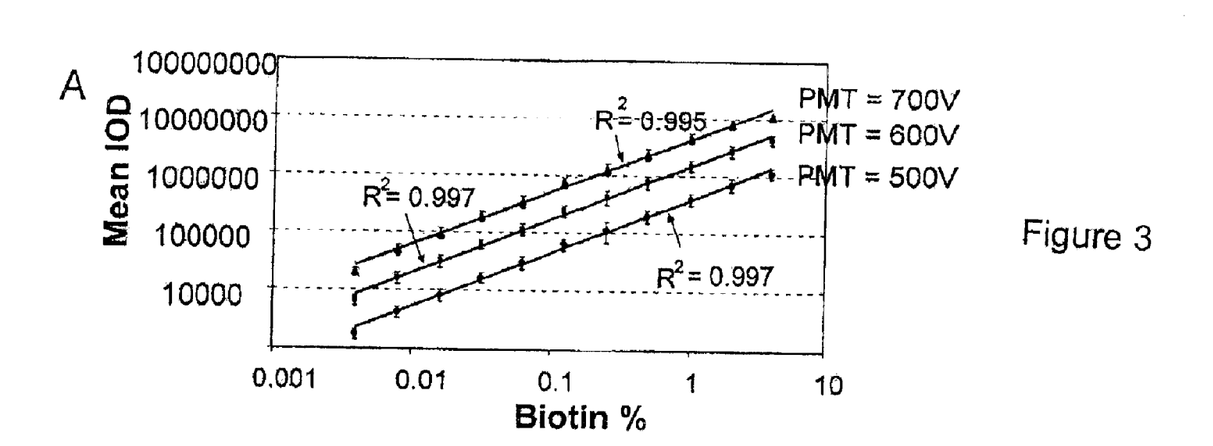
FIG. 3 shows data on the reproducibility and linearity of the streptavidin-fluorophore conjugate on biotin probe chips.
Figure 4:
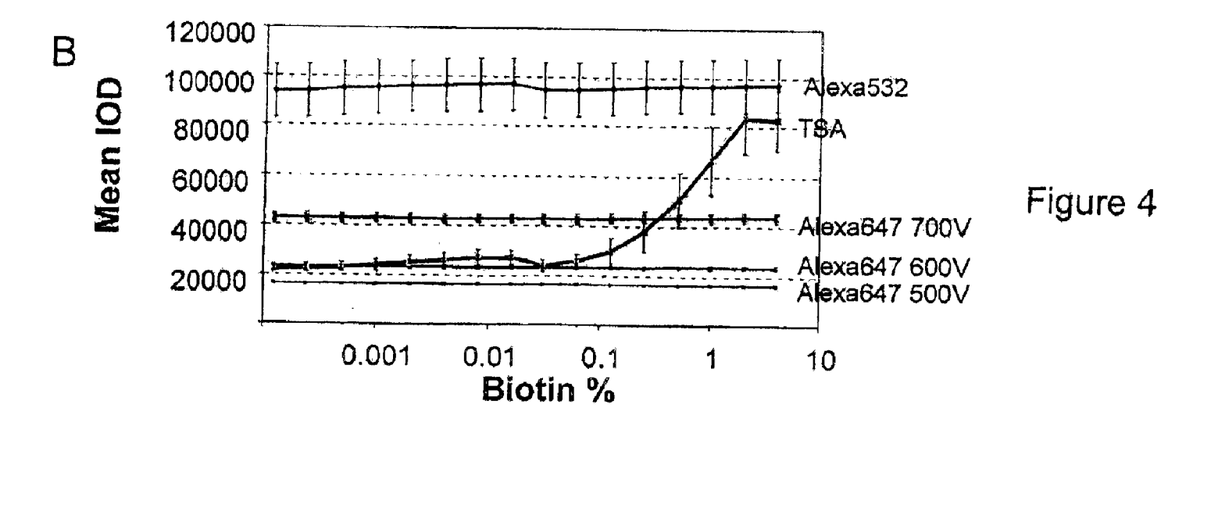
FIG. 4 shows the uniformity of the background for the streptavidin-ALEXA conjugate in relation to TSA detection methods.

Unlike TSA methods, linear methods do not rely on an additional active enzyme to incorporate fluorophores at the probe/target site. Typically, in linear methods, the fluorophore is incorporated into the streptavidin or avidin molecules. When the streptavidin or avidin binds to the biotin of probe bound target, fluorophores are directly incorporated at the site. While the streptavidin or avidin complexes may contain more than one fluorophore to generate a larger fluorescent signal, no further enzymatic fluorophore incorporation occurs. Thus, the fluorescent emission is no longer dependent on the variability of the enzyme reaction.

Because the current invention does not rely on enzymatic reactions to increase the amplitude of the fluorescent emission, but relies only on one streptavidin binding to each target, the invention produces fluorescent emissions demonstrating a more linear correlation between the number of hybridizations and emission amplitudes than TSA methods. This biotin/streptavidin binding system is especially suited to use on 3D hydrogel microarrays which show very high levels of background noise when TSA methods are used.

While biotin/streptavidin methods produce a more linear relationship between hybridized probe/target sites and emission amplitude on 3D hydrogels, signal amplitudes are not as great as for TSA methods due to the lack of the enzymatic amplification. The current invention overcomes this limitation through a multi-faceted approach.

A greater than one to one, most preferably four to one, correlation between fluorophores and targets is achieved because one to four fluorophores may be incorporated into a single streptavidin molecule. This results in up to a four to one amplification of fluorophores to hybridized targets.

Additional emission amplification may be obtained by adding a biotinylated anti-streptavidin antibody to the microarray after the streptavidin has bound at the hybridized probe/target sites. The biotinylated anti-streptavidin antibody binds to the streptavidin at each hybridized site, thus providing additional available biotins. Fluorophore labeled streptavidin may then be added which binds with the biotins of the anti-streptavidin antibody, thus incorporating additional fluorophores at the hybridized probe/target site. This process retains the linear relationship between hybridized targets and emission amplitude, but generates an increased emission amplitude. The method retains linearity because binding, not enzymatic, reactions are used to incorporate the fluorophores. This antibody amplification may be performed multiple times to further increase fluorescence amplitude if desired. A sample reaction sequence is as follows:

Probe/biotinylated target→SA*→Biotinylated Anti-SA antibody→SA*, where SA* represents streptavidin labeled with one or more fluorophores.

Emission amplitude may also be increased by using fluorophores with enhanced quantum yields, such as ALEXA-647, and by using fluorophores which absorb and emit at wavelengths which are not quenched by the hydrogel arrays or the biological molecules used when performing the analysis. Additionally, emission amplitude may be increased by fracturing the targets prior to hybridizing them with the probes. Preferably, the targets are fractured by heating in a magnesium solution to about 94° C. While not wishing to be bound by any particular theory, it is thought that by reducing the physical size of the labeled targets, their ability to diffuse across the surface of the microarray is improved.

Solid Support

Generally, the hydrogel is coated onto a solid support. Preferably, the "solid support" is any solid support that can serve as a support for the hydrogel, including film, glass, silica, modified silicon, ceramic, plastic, or polymers such as (poly)tetrafluoroethylene, or (poly)vinylidenedifluoride.

More preferably the solid support is a material selected from the group consisting of nylon, polystyrene, glass, latex, polypropylene, and activated cellulose. Most preferably, the solid support is glass.

The solid support can be any shape or size, and can exist as a separate entity or as an integral part of any apparatus, such as beads, cuvettes, plates, and vessels. If required, the support may be treated to provide adherence of the hydrogel to the glass, such as with γ-methacryl-oxypropyl-trimethoxysilane ("Bind Silane," Pharmacia). In particular, covalent linkage of polyacrylamide hydrogel to the solid support can be done as described in European Patent Application 0 226 470, incorporated by reference. The solid support may optionally contain electronic circuitry used in the detection of bit molecules, or microfluidics used in the transport of micromolecules.

Hydrogel

Preferably, the solid support is coated with a polyurethane or polyacrylamide hydrogel. Most preferably, the solid support is first coated with an acrylamide prepolymer, which may be coated and imaged using standard commercial equipment. The polyacrylamide prepolymer is non-toxic, easily handled, can be manufactured in highly consistent batches, and has good viscosity characteristics for coating surfaces during microarray manufacture.

Although further modification, including crosslinking and/or probe attachment, of the prepolymer is not required after synthesis, the prepolymer can be functionalized by the addition of one or more reactive sites. A detailed description of polyacrylamide hydrogels and hydrogel arrays made from polyacrylamide reactive prepolymers is given in WO 00/31148, entitled "Polyacrylamide Hydrogels and Hydrogel Arrays Made from Polyacrylamide Reactive Prepolymers," incorporated by reference.

Conversion of the prepolymer into a three-dimensional polyacrylamide hydrogel array, as preferred for the current invention, may entail additional steps, including developing the pattern in the array and removing any uncrosslinked polymer. Pattern development can be accomplished by exposing the reactive prepolymer through a photomask. Uncrosslinked polymer may also be removed by aqueous solution.

Preferably, the polymer is a polymer or copolymer made of at least two co-monomers that form a three-dimensional hydrogel, wherein at least one of the co-monomers can react by [2+2] photocycloaddition. Alternatively, the polymer is a polymer or copolymer that forms a three-dimensional hydrogel which is then chemically modified to contain a reactive site that undergoes [2+2] photocycloaddition.

Most preferably, the polymer is an acrylamide reactive prepolymer made by polymerizing acrylamide with a compound including dimethyl maleimide (DMI), a six carbon linker, and a polymerizable group, such as acrylate, to give a low molecular weight polymer. While not wishing to be bound by any particular theory, it is thought that when the reactive prepolymer is later crosslinked to form a three-dimensional hydrogel, the polymerizable group attaches to the acrylamide to form the hydrogel and the dimethyl maleimide attaches the resultant hydrogel to the solid support, and optionally to the probe if crosslinking and probe attachment are performed concurrently. During this process, it is believed that about 50% of the [2+2] photoreactive sites on the DMI remain available for probe attachment.

Probes

While probes may be attached to the hydrogel by chemical or thermal means, the most preferred method relies on [2+2] photocycloaddition between reactive sites on the hydrogel or reactive prepolymer and the probe. Preferable probes are antibodies, nucleic acids, or fragments thereof containing less than about 5000 nucleotides, especially less than about 1000 nucleotides and antibodies. Most preferably, a probe is an antibody or oligonucleotide, such as DNA or modifications thereof. Probes may be tissue or pathogen specific.

Preferably, probes inherently contain reactive sites or have been functionalized with a reactive site. Preferred probes requiring no further modification include certain nucleic acid species that incorporate pyrimidines such as thymine. Other preferred probes are modified to contain thymine or polythymine, or proteins incorporating thiols. A detailed description of suitable probes, reactive sites, and applicable probe modifications to allow [2+2] photocycloadditions is given in U.S. patent application Ser. No. 09/344, 620, filed Jun. 25, 1999, entitled "Method and Compositions for Attachment of Biomolecules to Solid Supports, Hydrogels and Hydrogel Arrays", incorporated by reference.

Reactive Sites

Antibodies or modified DNA oligonucleotides or polynucleotides are employed as probes that include a reactive site capable of undergoing [2+2] photocycloaddition. Additionally, the hydrogel polymer supports include reactive sites that are capable of undergoing [2+2] photocycloaddition. When irradiated with ultraviolet light at an appropriate wavelength, the probes are then attached to the hydrogel by [2+2] cycloaddition between the reactive sites. Typically the reactive site is introduced into the nucleic acid species by synthesizing or purchasing DNA functionalized with amine which is then reacted with the molecule having the desired reactive site to obtain DNA having the reactive site. Maleimide or acrylate functionalized DNA are examples. For protein arrays, one possible method to incorporate reactive sites involves the use of 5-(biotinamido) pentylamine (available from Pierce Chemical Co.) for attachment with the hydrogel matrix. This is followed by binding of streptavidin-conjugated antibodies specific for the protein of interest.

Preferable reactive sites may be provided by compounds including, dimethyl maleimide, maleimide, acrylate, acrylamide, vinyl, cinnamyl groups from cinnamic acid, cinnamate, chalcones, coumarin, citraconimide, electron deficient alkenes such as cyano alkene, nitro alkene, sulfonyl alkene, carbonyl alkene, arylnitro alkene, pyrimidine bases, thymine, and polythymine. Most preferred are acrylate, thymine, and dimethyl maleimide (DMI).

Reactive sites may be attached to the probe either directly or with an appropriate intermediate. A preferred intermediate is phosphoramidite. Most preferably, phosphoramidite is functionalized with a cinnamide and then attached to the oligonucleotide (5' position for DNA) to form a probe ready for [2+2] photocycloaddition. Other preferred reactive sites are as described in *Guillet*, "Polymer Photophysics and Photochemistry", Chapter 12 (Cambridge University Press: Cambridge, London).

Additionally, molecules having a structure similar to dimethyl maleimide may be employed to provide reactive sites on the probes, including maleimide/N-hydroxysuccinimide (NHS) ester derivatives. Such preferred maleimide/NHS esters include 3-maleimidoproprionic acid hydroxysuccinimide ester; 3-maleimidobenzoic acid N-hydroxy succinimide; N-succinimidyl 4-malimidobutyrate; N-succinimidyl 6-maleimidocaproate; N-succinimidyl 8-maleimidocaprylate; N-succinimidyl 11-maleimidoundecaoate. These esters can be obtained from a variety of commercial vendors, such as ALDRICH (Milwaukee, Wis.).

Reactive sites can yield homologous linking, where a probe reactive site cyclizes with a hydrogel reactive site having the same chemical structure, or for heterologous linking, where a probe reactive site cyclizes with a hydrogel reactive site having a different chemical structure. Preferred homologous linking occurs between DMI reactive sites on the probe and hydrogel, while preferred heterologous linking occurs between acrylate reactive sites on the probe and DMI reactive sites on the hydrogel. cDNA is a preferred probe for either type of cyclization.

[2+2] Photocycloaddition

According to the invention, "cyclization" or "photocycloaddition" is a light-induced reaction between two reactive groups, at least one of which is electronically excited. Advantageously, photocyclization reactions can be made to proceed with high efficiency. Photocycloaddition includes cyclodimerization and preferably includes [2+2] photocycloaddition. While it is chemical convention to write cycloaddition centers in brackets, such as "[2+2]" or "[4+2]," the brackets were omitted from the claims to prevent confusion with the patent convention of deleting bracketed material. Hence, in the claims "[2+2]" is written as "2+2". Preferably, photocycloaddition is of the [2+2] variety, wherein two carbon-carbon or carbon-heteroatom single bonds are formed in a single step. The [2+2] cycloaddition involves addition of a $2\pi$-component of a double bond to the $2\pi$-component of a second double bond. Alternatively, the reaction may proceed by way of a $2\pi$-component of triple bonds. Under the rules of orbital symmetry, such additions are thermally forbidden, but photochemically allowed. Such reactions typically proceed with a high degree of stereospecificity and regiospecificity.

Photochemical [2+2] cycloaddition of the probe to the hydrogel is obtained as follows. A reactive site is incorporated into the probe. A second reactive site is incorporated into the hydrogel following or as part of its polymerization, and prior to crosslinking. The combination is then irradiated with light at the appropriate wavelength to induce [2+2] photocycloaddition, which results in the probe being bound to the hydrogel. Optionally, a photosensitiser may be added to the hydrogel or reactive prepolymer to increase the efficiency of the photocycloaddition reaction. Preferred photosensitisers include water soluble quinones and xanthones, including anthroquinone, sulfonic acid quinone, benzoin ethers, acetophenones, benzoyl oximes, acylphosphines, benzophenones, and TEMED (N,N,N',N'-tetramethylethylendiamine). Anthroquinone-2-sulfonic acid is most preferred and is available from ALDRICH, Milwaukee, Wis.

Preferred [2+2] cycloadditions include those between two carbon-carbon double bonds to form cyclobutanes and those between alkenes and carbonyl groups to form oxetanes. Photocycloadditions between 2 alkenes to form cyclobutanes can be carried out by photo-sensitization with mercury or directly with short wavelength light, as described in Yamazaki et al., J. Am. Chem. Soc., 91, 520 (1969). The reaction works particularly well with electron-deficient double bonds because electron-poor olefins are less likely to undergo undesirable side reactions. Photocycloadditions between carbon-carbon and carbon-oxygen double bonds, such as $\alpha,\beta$-unsaturated ketones, form oxetanes (Weeden, In Synthetic Organic Photochemistry, Chapter 2, W. M. Hoorspool (ed.) Plenum, New York, 1984) and enone addition to alkynes (Cargill et al., J. Org. Chem., 36, 1423 (1971)).

EXAMPLES

The following examples are offered for illustrative purposes, and are not intended to limit the scope of the invention.

Example 1

Expression Arrays

Target preparation: Five micrograms of total RNA (BioChain, Hayward, Calif.) was added to a reaction mix in a final volume of 12 microliters, containing bacterial control mRNAs (2.5 pg/$\mu$l araBlentF, 8.33 pg/$\mu$l fixB/gnd and 25 pg/$\mu$l hisB/leuB), and 1.0 $\mu$l of 0.5 pmol/$\mu$l T7-(dT)$_{24}$ oligonucleotide primer. The mixture was incubated for 10 minutes at 70° C. and chilled on ice. With the mixture remaining on ice, 4 $\mu$l of 5×first-strand buffer, 2 $\mu$l 0.1 M DTT, 1 $\mu$l of 10 mM dNTP mix and 1 $\mu$l Superscript™ II RNaseH⁻ reverse transcriptase (200 U/$\mu$l) was added to make a final volume of 20 microliters, and the mixture incubated for one hour in a 42° C. water bath. Second-strand cDNA was synthesized in a final volume of 150 microliters, in a mixture containing 30 $\mu$l of 5×second-strand buffer, 3 $\mu$l of 10 mM dNTP mix, 4 $\mu$l of E. coli DNA polymerase I (10 U/$\mu$l) and 1 $\mu$l of RNase H (2 U/$\mu$l) for 2 hours at 16° C. The cDNA was purified using a Qiagen QIAquick purification kit, dried down, and resuspended in IVT reaction mix, containing 3.0 $\mu$l nuclease-free water, 4.0 $\mu$l 10×reaction buffer, 4.0 $\mu$l 75 mM ATP, 4.0 $\mu$l 75 mM GTP 3.0 $\mu$l 75 mM UTP, 3.0 $\mu$l 75 mM UTP, 7.5 $\mu$l 10 mM Biotin-11-CTP, 7.5 $\mu$l 10 mM Biotin 11-UTP and 4.0 $\mu$l enzyme mix. The reaction mix was incubated for 14 hours at 37° C. and CRNA target purified using an RNeasy® Kit (Qiagen). cRNA yield was quantitated by measuring the UV absorbance at 260 nm, and fragmented in 40 mM Tris-acetate (TrisOAc), pH 7.9, 100 mM KOAc, and 31.5 mM MgOAc, at 94° C., for 20 minutes. This typically resulted in fragmented target with a size range between 100–200 bases.

Post-hybridization processing using Streptavidin-ALEXA 647: The 12-slide holder was removed from the INNOVA 4080 shaker, and the hybridization chamber removed off each slide, using the Motorola Hybridization Chamber Removal Tool (Motorola Life Sciences). Each slide was briefly rinsed in TNT Buffer (0.1 M Tris-HCl, pH 7.6, 0.15 M NaCl, 0.05% Tween-20) at room temperature, and then washed in TNT buffer at 42° C. for 60 minutes. Signal was developed using a 1:500 dilution of streptavidin-ALEXA 647 (Molecular Probes), for 30 minutes at room temperature. Excess dye was removed, by washing four times with TNT Buffer, for 5 minutes each, at room temperature. Slides were rinsed in deionized water, and dried using a nitrogen gun. Processed slides were scanned using an AXON GENEPIX Scanner with the laser set to 635 nm, the PMT voltage to 600, and the scan resolution to 10 microns. Slides were scanned using CODELINK Scanning Software (Motorola Life Sciences), and images for each slide analyzed using the CODELINK Expression Analysis Software (Motorola Life Sciences).

Post-hybridization processing using the Tyramide Signal Amplification Technique: After hybridization, slides were briefly rinsed in TNT Buffer as previously described, and washed in TNT Buffer at 42° C. for 60 minutes. Slides were blocked in TNB Buffer (PE/NEN) for 30 min at room temperature, Each slide was then treated with 400 $\mu$l of streptavidin-HRP, diluted 1:200 in TNB, at room temperature for 30 minutes. Slides were washed 3 times, for 5 minutes each, in TNT Buffer. Signal was amplified using a 1:200 dilution of tyramide-Cy3 (PE/NEN) in Amplification Diluent Buffer (PE/NEN), for 5 min at room temperature. The reaction was stopped, and slides washed, by washing three times in TNT Buffer, for 5 min each, at room temperature. Slides were rinsed in deionized water, dried, scanned and analyzed as before.

Example 2 (Prophetic)

Protein Arrays

Protein labeling with biotin: Biotin derivatives designed to react with sulfhydryl groups (for example, on cysteine) or amino groups (for example, on lysine) are incubated with the protein mixture. After quenching of the reaction and purification (for example, on a streptavidin affinity column), the labeled protein mixture is ready for application on to the array of antibodies.

Binding of labeled proteins to the protein array: The labeled protein solution is dispersed onto the array and binding of the antibodies on the array to their respective proteins is allowed to occur. Washing of the array with a non-denaturing solution is next employed to eliminate any nonspecific binding. Each slide is briefly rinsed in TNT Buffer (0.1 M Tris-HCl, pH 7.6, 0.15 M NaCl, 0.05% Tween-20) at room temperature.

Detection of bound proteins with SA-ALEXA 647: Bound, labeled proteins are next detected by incubation with SA-ALEXA 647. Signal is developed using a 1:500 dilution of streptavidin-ALEXA 647 (Molecular Probes), for 30 minutes at room temperature. Excess dye is removed, by washing with TNT Buffer, for 5 minutes, at room temperature. Slides are rinsed in deionized water, and dried using a nitrogen gun. Processed slides are scanned using an AXON GENEPIX Scanner with the laser set to 635 nm, the PMT voltage to 600, and the scan resolution to 10 microns.

What is claimed:

1. A method of detecting a target nucleic acid or protein, comprising:
    (a) providing a target comprising a target nucleic acid or protein and a first member of a binding pair;
    (b) hybridizing the target nucleic acid or protein to a probe attached to a hydrogel matrix through a 2+2 photocycloaddition;
    (c) contacting the first member of the binding pair with a second member of the binding pair, said second member comprising a fluorophore; and
    (d) detecting the fluorophore additions, thereby detecting said target nucleic acid or protein.

2. The method of claim 1, wherein the first member comprises a first member selected from the group consisting of biotin, digoxygenin, and bromouridine.

3. The method of claim 2, wherein the first member comprises biotin.

4. The method of claim 1, wherein the second member is selected from the group consisting of avidin, streptavidin, biotin antibody, digoxygenin antibody, and bromouridine antibody.

5. The method of claim 4, wherein the second member comprises streptavidin.

6. The method of claim 1, wherein the nucleic acid is synthesized by producing a cDNA from a mRNA.

7. The method of claim 1, wherein the nucleic acid is synthesized by producing a cDNA or a cRNA from a DNA.

8. The method of claim 1, wherein the target is synthesized by incorporating the first member of a binding pair into the nucleic acid by polymerization.

9. The method of claim 1, wherein the protein is from a cell lysate.

10. The method of claim 1, wherein the hydrogel matrix comprises polyacrylamide.

11. The method of claim 1, wherein the hydrogel matrix comprises polyurethane.

12. The method of claim 1, wherein the probe comprises a reactive site capable of undergoing a 2+2 photocycloaddition.

13. The method of claim 1, wherein the hydrogel matrix comprises a reactive site capable of undergoing a 2+2 photocycloaddition.

14. The method of claim 5, wherein the streptavidin is attached to one or more fluorophores.

15. The method of claim 14, wherein the streptavidin is attached to between three and four fluorophores.

16. The method of claim 1, wherein said fluorophore is selected from the group consisting of cyanine dyes and ALEXA FLUOR dyes.

17. The method of claim 16, wherein the cyanine dye is Cy-3, Cy-5, or Cy-5.5.

18. The method of claim 16, wherein the ALEXA FLUOR dye is ALEXA-532, ALEXA-647, or ALEXA-633.

19. The method of claim 1, wherein said fluorophore is ALEXA-647.

20. The method of claim 1, further comprising contacting at least one of the second members of the binding pair with an antibody comprising a first member.

21. The method of claim 20, wherein the antibody is a biotinylated anti-streptavidin antibody.

22. The method of claim 20, wherein the first member comprises biotin and the second member comprises streptavidin attached to more than one fluorophore.

23. A method of detecting a single nucleotide polymorphism, comprising:
    (a) hybridizing a target nucleic acid to a probe attached to a hydrogel matrix through a 2+2 photocycloaddition, said probe designed to terminate at the site of the single nucleotide polymorphism;
    (b) extending the probe by one nucleotide, wherein the nucleotide comprises a first member of a binding pair;
    (c) contacting the first member of the binding pair with a second member of the binding pair comprising a fluorophore; and
    (d) detecting the fluorophore additions, thereby detecting the single nucleotide polymorphism.

24. The method of claim 23, wherein the nucleotide is a dideoxynucleotide or an acyclonucleotide.

25. The method of claim 23, wherein the nucleotide comprises the first member of the binding pair before said nucleotide is incorporated into the probe.

26. The method of claim 23, wherein the first member of the binding pair is attached to the nucleotide after incorporation of the nucleotide into the probe.

27. The method of claim 23, wherein the first member of the binding pair comprises biotin.

28. The method of claim 26, wherein the second member of the binding pair comprises streptavidin.

29. The method of claim 23, wherein the hydrogel matrix comprises polyacrylamide or polyurethane.

30. The method of claim 1, wherein the probe comprises a reactive site capable of undergoing a 2+2 photocycloaddition.

31. The method of claim 28, wherein the streptavidin is attached to more than one fluorophore.

32. The method of claim 23, wherein said fluorophore is selected from the group consisting of cyanine dyes and ALEXA FLUOR dyes.

33. The method of claim 32, wherein the cyanine dye is Cy-3, Cy-5, or Cy-5.5.

34. The method of claim 32, wherein the ALEXA FLUOR dye is ALEXA-532, ALEXA-647, or ALEXA-633.

35. The method of claim 23, wherein said fluorophore is ALEXA-647.

36. The method of claim 23, further comprising contacting at least one of the second members of the binding pair with an antibody comprising a first member.

37. The method of claim 36, wherein the antibody is a biotinylated anti-streptavidin antibody.

38. The method of claim 36, wherein the first member comprises biotin and the second member comprises streptavidin attached to more than one fluorophore.

* * * * *